United States Patent [19]

Richtzenhain et al.

[11] 4,111,902
[45] Sep. 5, 1978

[54] HEPTABROMODIBENZOFURAN, HIGHLY BROMINATED DIBENZOFURANS AND THE PREPARATION AND USE THEREOF AS FLAME RETARDANTS

[75] Inventors: Hermann Richtzenhain, Much-Schwellenbach; Klaus Schrage, Königswinter-Uthweiler, both of Fed. Rep. of Germany

[73] Assignee: Dynamit Nobel Aktiengesellschaft, Cologne, Fed. Rep. of Germany

[21] Appl. No.: 709,692

[22] Filed: Jul. 29, 1976

[30] Foreign Application Priority Data

Aug. 1, 1975 [DE] Fed. Rep. of Germany ....... 2534381

[51] Int. Cl.² .................. C08K 5/15; C07D 307/79
[52] U.S. Cl. .................. 260/45.8 A; 260/346.71
[58] Field of Search .......... 260/45.8 A, 346.2 M, 260/346.71

[56] References Cited

U.S. PATENT DOCUMENTS

3,935,251  1/1976  Dazzi et al. ............ 260/346.2 M

OTHER PUBLICATIONS

DOS 2513779 (Ube Industries, Japan), 9/10/1975.
Buser, Jour. Chromatography, vol. 107 (1975), pp. 295–310.

*Primary Examiner*—H.S. Cockeram
*Attorney, Agent, or Firm*—Burgess, Dinklage & Sprung

[57] ABSTRACT

Brominated dibenzofuran of the formula

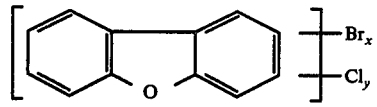

wherein $x + y = 6.0$ to $7.0$ and $y = 0$ to $0.3$. The brominated dibenzofuran can be prepared by reaction of bromine and dibenzofuran at 0° and 150° C in the presence of halogenation catalyst. The products are useful as flameproofing agents for organic polymers, e.g. polyethylene.

14 Claims, No Drawings

HEPTABROMODIBENZOFURAN, HIGHLY BROMINATED DIBENZOFURANS AND THE PREPARATION AND USE THEREOF AS FLAME RETARDANTS

BACKGROUND

The present invention describes the preparation of heptabromodibenzofuran and its use as a flameproofing agent. The subject matter of the invention is highly brominated dibenzofurans of the formula

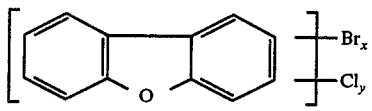

wherein $x + y = 6.0$ to $7.0$, preferably $6.5$ to $7.0$, and $y = 0$ to $0.3$. Particularly advantageous are highly brominated dibenzofurans having a bromine content equal to or greater than 75% by weight and a chlorine content equal to or less than 2% by weight. Additional subject matter is the new substance, heptabromodibenzofuran.

Highly brominated diphenyl ethers, such as octa- or decabromodiphenyl ether, have long been used as good flameproofing agents, especially in conjunction with synergists such as antimony oxide.

With regard to the cyclic ethers, only the tri- and tetrabromination of 2,4,8-trichlorodibenzofuran is known (German "Offenlegungsschrift" No. 2,411,665 of Ciba-Geigy AG), but a perbrominated dibenzofuran is unknown.

THE INVENTION

It has now been found that dibenzofuran can be reacted in solution to form heptabromodibenzofuran; an octabromodibenzofuran is impossible for steric reasons.

The bromination can be performed with elemental bromine (Example 1). For the sake of better utilization of the bromine, however, bromination with bromine chloride is preferred (Example 2), and it is surprising that chlorination, which usually occurs as an undesired secondary reaction in bromochlorinations, takes place to a very minor extent. The [Br] : [Cl] ratio in the product is greater than 20 if the bromochlorination is properly conducted. As will be shown in Example B, this provides an improved flameproofing action in the heptabromodibenzofuran prepared in accordance with the invention, in comparison to the formerly described tri- and tetrabromotrichlorodibenzofuran.

The brominating agent can be used in slight excess of the stoichiometric amount, preferably 20 to 30%. Excess bromine or bromine chloride is removed at the end of the bromination by the addition of unsaturated hydrocarbons, preferably ethylene.

The common metals or anhydrous metal halides can be used as halogenation catalysts; Fe and Fe(III) halides are preferred; aluminum and its halides, for example, can also be used. The catalyst concentration amounts to from 2 to 30 moles, preferably 10 to 20 moles, per hundred moles of dibenzofuran.

Halogenated hydrocarbons can be used as a reaction medium. The preferred solvent is 1,2-dichloroethane. *Upon the addition of only about one-third of the halogenating agent, a product begins to precipitate from the initially clear solution. The more highly brominated dibenzofurans are hardly soluble in common solvents, even in 1,2-dibromoethane. Amazingly, the bromination nevertheless results in a quantitative production of heptabromodibenzofuran in an economically reasonable reaction time.

Furthermore suitably are brominated solvents e.g. 1,2-dibromoethane, 1,3-dibromopropane. Also chlorinated solvents e.g. 1,1,2,2-tetrachloroethane, 1,1,1-trichloroethane, 1,2- and 1,3-dichloropropane, 1,1,3-trichloropropane are suitable, but in some cases a higher chlorine content then is effected in the product.

The bromination with bromine is performed preferably at the refluxing temperature of the solvent. In the case of bromination with bromine chloride it has proven to be advantageous to feed in the bromine chloride while cooling the reaction mixture, and only thereafter to increase the reaction temperature slowly. The reaction temperature accordingly lies generally between 0° and 150° C., preferably between 10° and 80° C.

The dibenzofuran produced in the distillation of coal tar, for which no very great technical application has been found previously, serves as the raw material. In contrast to the exceedingly toxic, teratogenic and chloracne causing trichlorodibenzofuran (H. Bauer et al., Arch. Gewerbepath. Gewerbehyg. 18, 538 (1961) and V. Zitko, P.M.K. Choi, Bull. Environmental Contamination and Toxicology 10 (2) 120 (1973), which is used as starting substance in the preparation of highly halogenated dibenzofurans in accordance with the abovementioned "Offenlegungsschrift", dibenzofuran requires no special precautions in handling. Heptabromodibenzofuran, when subjected to toxicological tests (FDA standards), gave the following results:

(1) $LD_{50}$ in mice: Test discontinued after administration of 10 g of heptabromodibenzofuran per kilogram of mouse. A dose of 10 g/kg of mouse did not lead to the death of the animals.

(2) Skin irritation test (Draise - skin) in the rabbit, and Mucosa irritation test (Draise - eye) in the rabbit: In neither of these tests were reactions observed in any animal after administration of the preparation.

The mother liquor from the bromination can be reused very economically for the next batch after the reaction product has been separated. This has the additional advantage that any low-brominated, possibly toxic dibenzofurans contained in the mother liquor do not have to be processed. Recycling of the mother liquor has been tested up to eight times without any decrease in reaction speed, change in product composition, or any other kind of impairment.

The brominated dibenzofurans prepared in accordance with the invention are outstandingly suitable as flame-proofing agents for organic polymers (Examples A to D), whether they be addition polymers or condensation polymers, and for unreinforced products and products reinforced with glass fibers, for example, and also for fibers and raw materials for the production of fibers, as well as lacquers etc. Such polymers include preferentially homopolymers and copolymers of olefins including styrene; polystryene and its copolymers and graft polymers with, for example, butadiene and/or acrylonitrile or with methacrylic acid esters; polyesters, both on the basis of α,w-lactones and on the basis of glycols and dicarboxylic acids of the aromatic and aliphatic series. Polyamides polyacrylonitrile, epoxy resins and phenolic resins, unsaturated polyesters, and other polymerization and polycondensation synthetic products can also be made flame-resistant by highly brominated dibenzofurans. By reason of their extraordinary thermostability, highly brominated dibenzofurans are especially suited for those high polymers which must be worked at high temperatures. Their compatibility is good, and their volatility is low on account of their high molecular weight.

Additional subject matter of the invention is therefore flameproofed plastic compositions with contents of highly brominated dibenzofurans in accordance with the foregoing structural formula, preferably having a bromine content of 75 wt.-% or more and a chlorine content of 2 wt.-% or less as flameproofing agents, in amounts of 1 to 30 wt.-%, preferably 5 to 15 wt.-%.

The brominated dibenzofurans are admixed with the polymers by conventional methods. The addition of synergists, especially antimony trioxide, is advantageous. The most effective weight ratio of flameproofing agent to antimony trioxide is between 2 : 1 and 10 : 1, depending on the nature of the polymer. Other additives, especially glass fibers, can be used without negative effect on the flame-proofing action.

EXAMPLES

EXAMPLE 1

In a three-necked flask equipped with stirrer, reflux condenser and dropping funnel, 281 grams (1.76 moles) of bromine are added drop by drop, over a period of 3 hours, to a boiling solution of 33.6 g (0.2 mole) of dibenzofuran and 3.2 g (0.02 moles) of $FeCl_3$ in 500 ml of 1,2-dichloroethane. After the addition of the bromine, the mixture was refluxed for another 3 hours. Then ethylene was introduced until the reflux was colorless, to remove excess bromine.

After the cooling of the reaction mixture the product was suction filtered, stirred up in 250 ml of 1,2-dichloroethane, and again suction filtered. After drying, 141 g of product is obtained with a melting point of 303°–309° C.

| Analysis shows: $C_{12}HOCl_{0.2}Br_{6.8}$ | | | | | |
|---|---|---|---|---|---|
| Calculated: | C 20.2 | H 0.1 | O 2.3 | Cl 1.0 | Br 76.4 |
| Found: | C 19.8 | H 0.1 | O 2.5 | Cl 1.3 | Br 76.3 |

The utilization of the bromine put in was 39%, and that of the benzofuran was nearly 100%.

In like manner, by using 4.6 g (0.03 moles) of $FeCl_3$ as catalyst in boiling 1,2-dibromoethane, 140 grams of a product are obtained which has a melting point of 308°–310° C. and has the following composition:

| $C_{12}HOBr_7$ | Calc.: | C | 20.0 | H | 0.1 | 0 | 2.2 | Br | 77.6 |
|---|---|---|---|---|---|---|---|---|---|
| | Found: | | 19.7 | | 0.2 | | 2.3 | | 77.2 |

The utilization of the bromine put in amounted to 38%, and that of the dibenzofuran 98%.

The products turn brown on exposure to air on account of their residual iron content. By boiling them with methanolic hydrochloric acid ($H_2O$ : $CH_3OH$ : conc. HCl = 80 : 10 : 10 ml) one obtains a colorless, iron-free powder.

EXAMPLE 2

In a four-necked flask with stirrer, a reflux condenser, a cooled dropping funnel, and a thermometer, and containing 33.6 g (0.2 moles) of dibenzofuran and 3.2 g (0.02 moles) of $FeBr_3$ in 500 ml of 1,2-dichloroethane, 222 g (1.92 moles) of bromine chloride is added over a period of two hours while the temperature within the flask is maintained at 15° C. by external cooling. The bromine chloride is previously prepared in the dropping funnel by the introduction of 68 g of chlorine into 154 g of cooled bromine. The reaction mixture is then refluxed for three hours. After removal of the excess bromine by the introduction of ethylene and the cooling of the mixture, the product is suction filtered. The product is then stirred with 250 ml of 1,2-dichloroethane and again suction filtered. The mother liquor and the 1,2-dichloroethane used for the washing are combined and concentrated by evaporation to 500 ml; then 1.6 to 2.4 g (0.01 to 0.015 moles) of $FeCl_3$ is added, and the mixture is used for the next batch.

From a total of five identical batches processed with the mother liquor from each preceding operation, one thus obtains, from 168 g (1.0 mole) of dibenzofuran and 1100 g (9.5 moles) of bromine chloride, 695 grams of a product having a melting point of 300° to 303° C. and the composition $C_{12}H_{1.1}OCl_{0.3}Br_{6.6}$:

| Calc.: | C | 20.6 | H | 0.2 | O | 2.3 | Cl | 1.5 | Br | 75.4 |
|---|---|---|---|---|---|---|---|---|---|---|
| Found: | | 20.5 | | 0.2 | | 2.5 | | 1.4 | | 75.5 |

Accordingly, the utilization of the bromine put in amounts to 69%, and that of the dibenzofuran to virtually 100%.

EXAMPLE A (Use)

100 g of polyethylene (Hostalen GF 7750, Hoechst AG) is mixed for 12 minutes on a two-roll mixer at 150° C. with the amounts stated in the Table of brominated dibenzofuran and antimony oxide. A board is pressed in 3 minutes at 140° C. from the skin cut from the roller mixer, and from it specimens are cut for the measurement of the "Lowest Oxygen Index" (LOI) in accordance with ASTM D 2863-70. The LOI value indicates how high the oxygen concentration must be in an oxygen-nitrogen mixture to enable a specimen of the flameproofed plastic to barely burn at room temperature. A higher flameproofing action on the part of the flameproofing agent incorporated is expressed in a higher LOI value or in a greater difference in the LOI value in comparison to that of the standard specimen.

| x | y | Flame proofing agent in grams per 100 g of polyethylene | $Sb_2O_3$ in grams per 100 g of polyethylene | LOI ASTM D 2863 | Δ LOI |
|---|---|---|---|---|---|
| — | — | none | none | 17 | — |
| 6.2 | — | 9 | 2 | 27 | 10 |
| | | 9 | 4 | 27 | 10 |
| | | 6 | 2 | 26 | 9 |

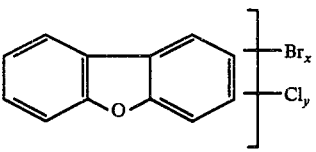

| x | y | Flame proofing agent in grams per 100 g of polyethylene | Sb$_2$O$_3$ in grams per 100 g of polyethylene | LOI ASTM D 2863 | Δ LOI |
|---|---|---|---|---|---|
| 6.5 | — | 9 | 4 | 27 | 10 |

Example B 100 g of polypropylene (PPM 1060, Hoechst AG) is mixed on a two-roll mixer for 12 minutes at 180° C. with the amounts stated in the Table of brominated dibenzofuran and antimony oxide. The skin cut from the roll is used for the pressing of a board at 140° C. for 3 minutes, from which specimens are cut for measurements of the LOI according to ASTM D 2863-70.

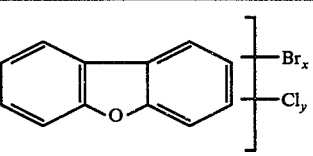

| x | y | Flame proofing agent in grams per 100 g of polypropylene | Sb$_2$O$_3$ in grams per 100 g of polyethylene | LOI ASTM D 863 | Δ LOI |
|---|---|---|---|---|---|
| — | — | none | none | 17 | — |
| 6.8 | 0.2 | 10 | 2 | 22 | 5 |
|  |  | 6 | 2 | 22 | 5 |

For comparison Example 6 from German "Offenlegungsschrift" 2,411,665 of Ciba-Geigy AG:

| | | | | | |
|---|---|---|---|---|---|
| — | — | none | none | 18 | — |
| 4 | 3 | 10 | 2 | 21 | 3 |

Example C 100 g of polystyrene (432 F, BASF) is mixed on a two-roll mixer for 12 minutes at 180° C. with the amounts stated in the table of brominated dibenzofuran and antimony oxide. The skin cut from the roller was pressed at 170° C. for 3 minutes to produce a board from which specimens were cut for measurments of the LOI according to ASTM D 2863-70.

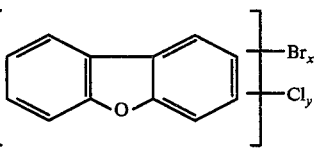

| x | y | Flameproofing agent in grams per 100 g of polystyrene | Sb$_2$O$_3$ in grams per 100 g of polystyrene | LOI ASTM D 2863 | Δ LOI |
|---|---|---|---|---|---|
| — | — | none | none | 17 | — |
| 6.8 | 0.2 | 12 | 5 | 24 | 7 |
|  |  | 9 | 4 | 22 | 5 |
|  |  | 6 | 4 | 21 | 4 |

Example D 100 parts of polybutyleneterephthalate (Dynamit Nobel AG) with a reduced viscosity of 1.4 were mixed with 9 parts of heptabromodibenzofuran and 4 parts of antimony oxide and injection molded to form test specimens for measurement of the LOI pursuant to ASTM D 2863-70. In comparison to an LOI of 20 without additives, the LOI of the polyester treated with flameproofing agent was 30.

In like manner, 100 parts of polyethyleneterephthalate (Dynamit Nobel AG) of a reduced viscosity of 1.2 was mixed with 9 parts of the flameproofing agent of Example C and 4 parts of antimony oxide, and a considerable increase of the LOI was found in comparison with the untreated specimen.

What is claimed is:

1. Brominated dibenzofuran of the formula

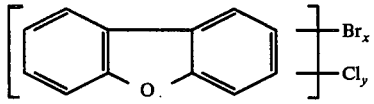

wherein $x + y = 6.0$ to $7.0$ and $y = 0$ to $0.3$.

2. Brominated dibenzofuran of claim 1, wherein $x + y = 6.5$ to $7.0$.

3. Process for the preparation of the brominated dibenzofuran of the formula

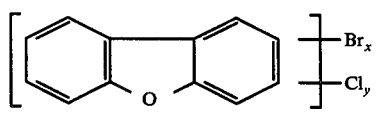

wherein $x + y = 6.0$ to $7.0$ and $y = 0$ to $0.3$ comprising reacting dibenzofuran with bromine at from 0° to 150° C. in the presence of halogenation catalyst.

4. Process of claim 3, wherein the bromine is in the form of bromine chloride.

5. Process of claim 3, wherein the catalyst is at least one of Fe, Fe(III) halide, Al, or Al halide.

6. Process of claim 3, wherein the reaction is performed in the presence of a halogenated hydrocarbon as a reaction medium.

7. Process of claim 3, wherein the bromine is in the form of bromine chloride, the catalyst is at least one of Fe, Fe(III) halide, Al, or Al halide, and the reacting is performed in the presence of a halogenated hydrocarbon as a reaction medium.

8. Flameproofed organic polymer composition containing brominated dibenzofuran of claim 1 in amount of 1–30 wt.% to improve the flameproofness of the polymer.

9. Flameproofed organic polymer composition of claim 8, and antimony trioxide for improving the flameproofness in a weight ratio of brominated dibenzofuran to antimony trioxide of from 2:1 to 10:1.

10. Flameproofed organic polymer composition of claim 8, the polymer being a homopolymer or copolymer of olefin.

11. Flameproofed organic polymer composition of claim 8, the polymer being a homopolymer or copolymer of styrene.

12. Flameproofed organic polymer composition of claim 8, the polymer being a linear polyester.

13. Flameproofed organic polymer composition of claim 8, the polymer being filled with glass fibers.

14. Brominated dibenzofuran of claim 1 wherein $x$ is 7.

* * * * *

UNITED STATES PATENT AND TRADEMARK OFFICE
CERTIFICATE OF CORRECTION

PATENT NO. : 4,111,902
DATED : September 5, 1978
INVENTOR(S) : Hermann Richtzenhain and Klaus Schrage It is certified that error appears in the above-identified patent and that said Letters Patent are hereby corrected as shown below:

Col. 2, line 35, before "Mucosa" insert --(3)--.

Col. 5, Example B, Title, 4th col., change "polyethylene" to --polypropylene--.

Col. 5, Example B, Title, 5th col., change "863" to --2863--.

Col. 7, line 5, change "reaction" to --reacting--.

Signed and Sealed this

Third Day of April 1979

[SEAL]

Attest:

RUTH C. MASON
*Attesting Officer*

DONALD W. BANNER
*Commissioner of Patents and Trademarks*